United States Patent [19]

Carter et al.

[11] 4,056,116

[45] Nov. 1, 1977

[54] VALVE FOR INTERCONNECTING STERILE CONTAINERS AND THE LIKE

[75] Inventors: Garry L. Carter, Palatine; Daniel B. Granzow, Arlington Heights, both of Ill.

[73] Assignee: Baxter Travenol Laboratories, Inc., Deerfield, Ill.

[21] Appl. No.: 721,622

[22] Filed: Sept. 8, 1976

[51] Int. Cl.$^2$ ............................................. A61M 5/14
[52] U.S. Cl. ............................ 137/68 R; 128/214.2; 128/247; 251/342
[58] Field of Search .................... 137/68 R, 318; 128/214 R, 214 D, 214.2, 247; 285/3; 222/83; 251/342

[56] References Cited

U.S. PATENT DOCUMENTS

| | | | |
|---|---|---|---|
| 2,667,760 | 2/1954 | Curtis | 137/68 R X |
| 2,829,801 | 4/1958 | Ayres | 222/83 X |
| 3,110,308 | 11/1963 | Bellamy | 128/214 D |
| 3,448,779 | 6/1969 | Horwitt | 137/318 X |
| 3,648,693 | 3/1972 | Koremura | 128/214 D |
| 3,685,795 | 8/1972 | Caster | 251/342 |

FOREIGN PATENT DOCUMENTS 1,528,025  4/1968  France ............................. 128/214 D

*Primary Examiner*—Martin P. Schwadron
*Assistant Examiner*—Richard Gerard
*Attorney, Agent, or Firm*—Henry W. Collins; Paul C. Flattery; Garrettson Ellis

[57] ABSTRACT

A sealed fluid conduit, closed with a diaphragm, contains a spike having forward and rear ends and adapted for moving to rupture the diaphragm with the forward end. A transversely-enlarged, flexible, axially collapsible portion of the conduit is positioned adjacent to the spike and adapted to permit manual movement of the spike from outside of the conduit to rupture the diaphragm. In accordance with this invention, a longitudinal groove is defined in the spike extending from the front end and terminating at a point between the front and rear ends. The spike defines an annular, enlarged sealing portion of a transverse dimension which is proportioned to sealingly occlude the portion of the conduit immediately forward of the transversely enlarged collapsible portion, the sealing portion being positioned between the terminating point of the groove and the rear end of the spike. The spike is positioned so that the enlarged sealing portion normally resides within the transversely-enlarged collapsible portion.

7 Claims, 5 Drawing Figures

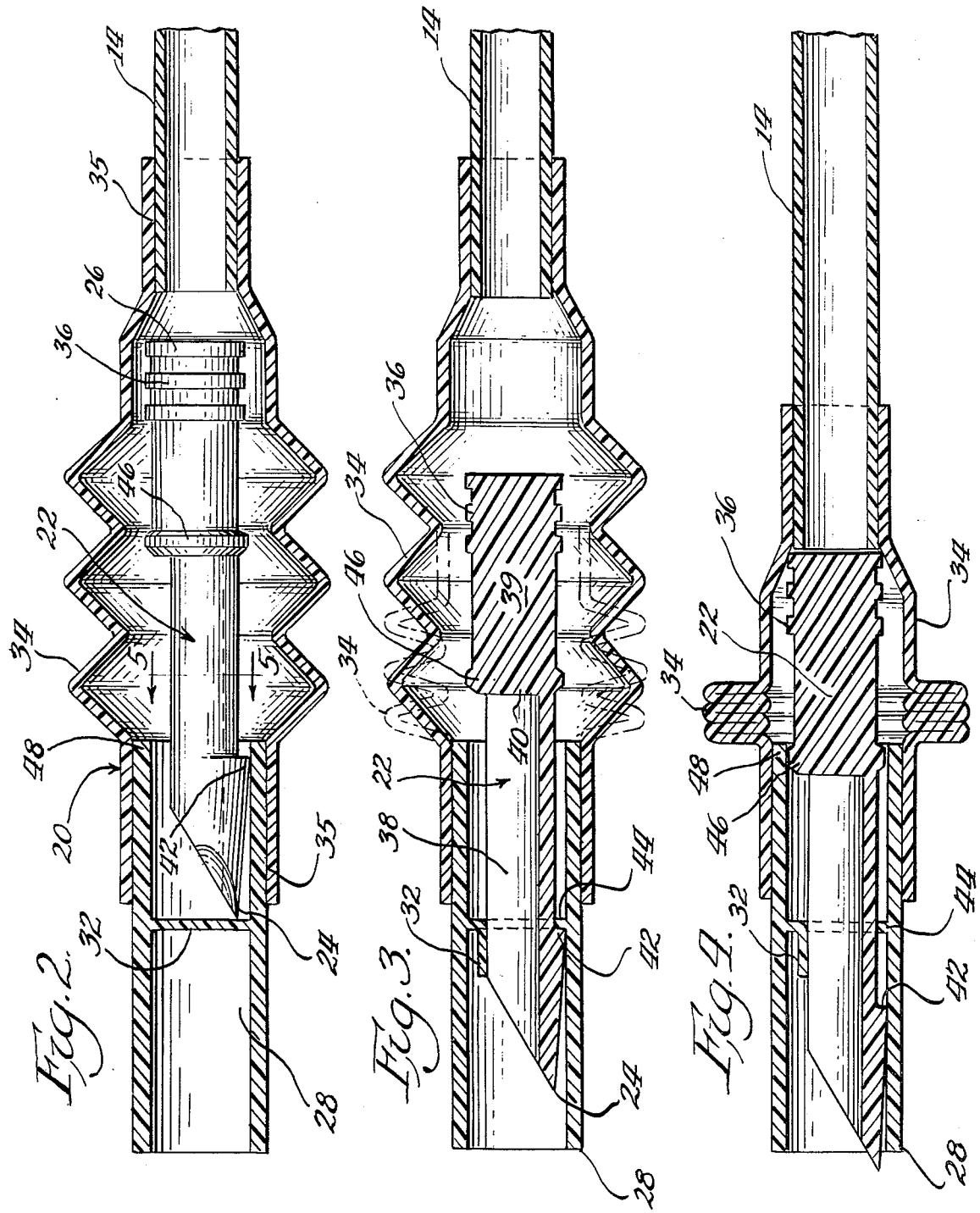

VALVE FOR INTERCONNECTING STERILE CONTAINERS AND THE LIKE

BACKGROUND OF THE INVENTION

Interconnecting multiple blood bags are sold for the collection of blood under sterile conditions and then for the processing of the various blood components through centrifugation, followed by expulsion of the components such as blood plasma from the original bag, in which the blood is collected, to a transfer bag through connecting tubing.

Generally, a valve means is used to close the tubing between the two bags until the transfer operation is to take place. Thereafter it is once again desirable to close the communication by means of a valve.

In U.S. Pat. No. 3,685,795 a cannula valve is disclosed comprising a spike for puncturing a diaphragm to open the flow path, and also providing other valving means for reclosing the path again as desired. However, this structure must be collapsed to rupture the diaphragm, and then must be reextended again to open the flow path. Also, the components of the device are rather expensive and difficult to assemble. Likewise, upon withdrawal of the spike from the membrane area, the flap of the punctured membrane may swing out into transverse relation to the tubing, again blocking flow through the tubing and the valve.

U.S. Pat. No. 3,110,308 discloses a hollow cannula which is separate from and free-floating in the bore of tubing, passing between a pair of sterile medical fluid containers. This free-floating cannula can be manipulated forwardly from the outside to puncture a diaphragm. However, the structure provides no capability for resealing of that device.

The structure of this invention exhibits a novel valve system utilizing a membrane for initial sealing and a cannula for initial opening, and providing a resealing capability, plus means for prevention of the ruptured membrane swinging back to obstruct the flow path through the tubing in which it resides.

The device of this invention provides an open valve immediately after penetration of the diaphragm, without withdrawing, while still permitting resealing of the valve.

DESCRIPTION OF THE INVENTION

The invention of this application is utilized in a sealed tubular fluid conduit having a diaphragm positioned to block fluid flow through the conduit. The conduit includes a spike having front and rear ends mounted in the fluid conduit and adapted for movement to rupture the diaphragm with its front end. A transversely-enlarged, flexible, axially collapsible portion of the conduit is positioned adjacent to the spike and adapted to permit manual movement of the spike from outside of the conduit to rupture the diaphragm.

In accordance with this invention, a longitudinal groove is defined in the spike extending from its front end and terminating at a point between the front and rear ends. The spike also defines an annular, enlarged sealing portion of a transverse dimension which is proportioned to sealingly occlude a portion of the conduit immediately forward of the transversely-enlarged, collapsible portion. The sealing portion is positioned between the terminating point of the groove and the rear end of the spike. The spike is positioned so that the enlarged sealing portion normally resides within the transversely-enlarged, collapsible portion of the conduit. Accordingly, for resealing of the conduit after rupture of the diaphragm, the spike may be moved to bring the enlarged sealing portion into flow-blocking relation in the conduit immediately forward of the transversely-enlarged portion.

Correspondingly, the valve may be opened again by withdrawing the spike so that the sealing portion moves out of engagement with the conduit portion immediately forward of the transversely-enlarged portion.

Preferably, in both positions of the spike for permitting flow or preventing flow through the conduit, the spike remains in a position penetrating the diaphragm. Accordingly, the diaphragm is held by the spike against the side of the conduit, and cannot swing outwardly to obstruct the flow therethrough.

The front end of the spike typically defines a point, behind which is positioned a projection extending laterally outwardly beyond the point. This projection is utilized to engage a stub portion of the diaphragm which remains after penetration by the spike, so that the accidental withdrawal of the spike from penetrating relationship with the diaphragm is resisted.

It is preferred for the spike to be free from mechanical connection with the conduit, so that after advancement of the spike, the axially collapsible portion of the fluid conduit can once again reexpand, without urging the spike to withdraw from its membrane-piercing position.

In the drawings,

FIG. 2 is an enlarged longitudinal sectional view of the valve of this invention, with the spike shown in elevation, prior to initial opening of the valve.

FIG. 3 is a longitudinal sectional view of the valve of FIG. 2, showing the spike in longitudinal section, after opening of the valve to permit flow therethrough.

FIG. 4 is a longitudinal sectional view of the valve of FIG. 3 showing the valve in its closed configuration after initial opening.

Figure 1:
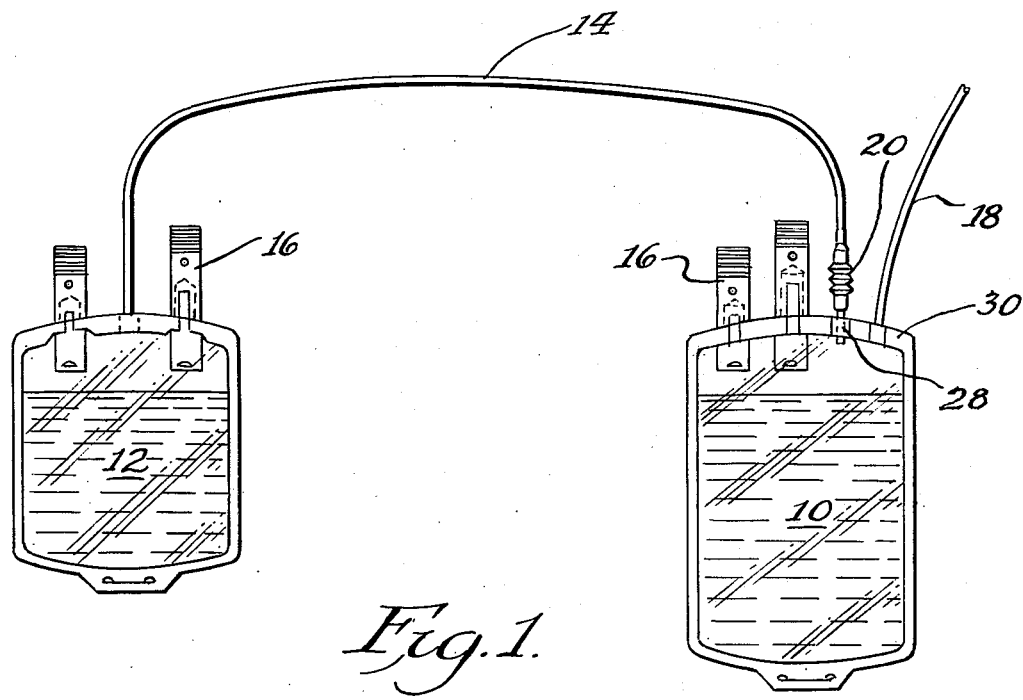
FIG. 1 is an elevational view of a pair of interconnected blood bags, utilizing the cannula valve of this invention.
Figure 5:
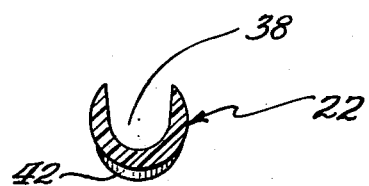
FIG. 5 is a transverse sectional view taken along line 5—5 of FIG. 2.

Referring to the drawings, a pair of blood bags 10, 12 are connected together by tubing 14 to form a conventional double bag. It is of course understood that other uses may be made of the valve of this invention, apart from its use in a double bag for blood collection and processing. For example, it may be used in triple and quadruple bags, or in conjunction with parenteral solution containers, drainage fluid collection containers, and the like.

Donor tube 18 typically carries a blood collection needle for collecting a unit of blood from the patient.

Outlet ports 16 are customarily sealed as indicated in a conventional manner until desired for use.

Valve 20 may be positioned at one end of tube 14 as shown, to seal the contents of bag 10 until the sterile transfer of a portion of the contents to bag 12 is desired. Thereafter, valve 20 can be reclosed.

FIG. 2 is an enlarged view of valve 20, prior to its initial opening. Valve 20 includes a spike 22 which defines a pointed front end 24 and a rear end 26. A conduit section 28 is provided, being retained in the heat sealed periphery 30 of bag 10, and defining a diaphragm 32.

Spike 22 is carried within the fluid conduit defined by section 28, flexible tubing 14, and bellows member 34, which is a transversely-enlarged, flexible, axially-collapsible portion of the conduit. Members 14, 34, and 28 may be conventionally sealed together at their ends in telescoping relation, as shown.

FIG. 3 shows how spike 22 may be advanced to rupture diaphragm 32 with its point 24. This is generally accomplished by grasping the exterior of bellows member 34 about flanges 36 of the spike, which are provided as friction members to facilitate grasping and manipulating of the spike from outside of the conduit. The spike is manually advanced to pierce diaphragm 32, facilitated by the collapsing of bellows member 34 as shown in FIG. 2 in phantom lines. Thereafter, upon release of the bellows member 34, it may spring back to its original position without pulling spike 22 out of position.

Spike 22 defines a longitudinal groove 38 extending from front end 24 and terminating at a point 40 between the front and rear ends.

As shown in FIG. 3, when spike 22 is advanced to the degree shown, a fluid flow path is opened through groove 38, and then around the solid portion 39 of spike 22, within bellows member 34, to tubing 14, through which communication with bag 12 is achieved.

Pointed front end 24 is so proportioned that the point of spike 22 defined at the front end is spaced laterally inwardly by a small distance from projection 42 of the spike, which is positioned rearwardly of pointed front end 24. Accordingly, when spike 22 penetrates diaphragm 32, the cut by the pointed end 24 through the diaphragm 32 is slightly spaced from the inner wall of tubular section 28, as shown in FIG. 3, to define diaphragm stub 44.

Accordingly, projection 42 can engage diaphragm stub 44. This engagement between projection 42 and diaphragm stub 44 provides a detent relationship which reduces the likelihood of accidental withdrawal of spike 22.

As a further advantage of the structure of this invention, diaphragm 32 is prevented by spike 22 from swinging outwardly to obstruct once again the flow through tubular section 28.

Spike 22 also defines an annular, enlarged sealing portion 46 having a transverse dimension which is proportioned to sealingly occlude portion 48 of the conduit, which is immediately forward of the transversely-enlarged, collapsible portion 34. This relationship is achieved, as shown in FIG. 4, by gripping the collapsible portion 34 about flanges 36 of the spike, and advancing spike 22 farther into tubular member 28 until annular, enlarged portion 46 seals the conduit bore in the vicinity of area 48, immediately forward of the enlarged, collapsible bellows portion 34. Thus the valve is closed.

To open the valve, one can manually grip and collapse collapsible portion 34, and thus grip flanges 36, to withdraw spike 22 once again to the FIG. 3 configuration. The engagement of projection 42 with diaphragm stub 44 provides a resistance to further rearward movement of the spike, which can be sensed by the user as an indication that the spike has been withdrawn into flow-permitting relationship. In this position, diaphragm 32 is held out of flow-restricting relationship.

Because the valve of this invention does not utilize a solid point, it can be made shorter, with a shorter stroke length for spike 22 than other resealing cannula valves. This results in lower material and packaging costs, as well as providing a more reliable functioning, since the remains of diaphragm 32 are positively held out of flow-restricting position.

The above has been offered for illustrative purposes only, and is not for the purpose of restricting the scope of the invention of this application, which is as defined in the claims below.

That which is claimed is:

1. In a sealed, tubular fluid conduit having a diaphragm positioned to block fluid flow through said conduit, said fluid conduit carrying a spike having front and rear ends positioned in said fluid conduit and adapted for movement to rupture said diaphragm with said front end, and a transversely-enlarged, flexible, axially-collapsible portion of said conduit positioned adjacent said spike and adapted to permit manual movement of said spike from outside of said conduit to rupture said diaphragm, the improvement comprising, in combination:

a longitudinal groove defined in said spike extending from said front end and terminating at a point between said front and rear ends, said spike also defining an annular, enlarged sealing portion of a transverse dimension which is proportioned to sealingly occlude a portion of said conduit adjacent to said transversely-enlarged, collapsible portion, said sealing portion being positioned between said terminating point of the groove and the rear end of the spike, said spike being positioned so that said enlarged sealing portion normally resides within said transversely-enlarged collapsible portion, said spike and conduit being dimensioned such that upon rupture of the diaphragm a flow path is defined through said groove and about said enlarged seal portion, whereby, for resealing said conduit after rupture of the diaphragm, the spike may be moved to bring said enlarged sealing portion into flow-blocking relation with said conduit immediately adjacent to said transversely-enlarged portion.

2. The device of claim 1 in which said spike defines a projection positioned and extending laterally outwardly in a position adjacent to said front end and adapted to engage a stub portion of the diaphragm which remains after penetration by said front end, to prevent accidental withdrawal of the spike from penetrating relationship with the diaphragm.

3. The device of claim 2 in which the front end of said spike defines a point positioned laterally inwardly from said projection.

4. The apparatus of claim 3 in which said spike is proportioned to both permit and prevent fluid flow through said conduit by alteration of the longitudinal position of the spike, while remaining in diaphragm-penetrating position, to hold said diaphragm against the side of the conduit.

5. The device of claim 4 in which said spike is free from mechanical connection with said conduit.

6. The device of claim 5 in which said rear end of the spike carries friction member means to facilitate grasping and manipulating of the spike from outside of said conduit.

7. The device of claim 6 in which said transversely-enlarged, flexible, axially collapsible portion of the conduit is defined by a bellows member sealingly attached at both ends to other portions of said conduit.

* * * * *